US006437345B1

(12) United States Patent
Bruno-Raimondi et al.

(10) Patent No.: US 6,437,345 B1
(45) Date of Patent: Aug. 20, 2002

(54) SENSING UNIT PROVIDED WITH SEPARATED DETECTION LIGHT GUIDING

(75) Inventors: Alfredo Emilio Bruno-Raimondi, Biel-Benken; Reinhard Völkel, Neuchâtel, both of (CH); Gert Ludwig Duveneck, Bad Krozingen; Carlo Stefan Effenhauser, Weinheim, both of (DE); Hans-Peter Herzig, Neuchâtel; RenéDändliker, Corcelles, both of (CH)

(73) Assignee: Zeptosens AG, Witterswil (CH)

( * ) Notice: Subject to any disclaimer, the term of this patent is extended or adjusted under 35 U.S.C. 154(b) by 0 days.

(21) Appl. No.: 09/711,294

(22) Filed: Nov. 14, 2000

Related U.S. Application Data (63) Continuation of application No. PCT/EP99/03296, filed on May 12, 1999.

(30) Foreign Application Priority Data

May 14, 1998 (GB) ................................. 9810350

(51) Int. Cl.$^7$ ............................................... G01N 21/64
(52) U.S. Cl. .................................. 250/458.1; 250/252.1
(58) Field of Search ........................... 250/458.1, 252.1, 250/222.2, 339.07, 339.09, 461.1; 356/318

(56) References Cited

FOREIGN PATENT DOCUMENTS

| DE | 36 18 605 | 12/1987 | |
|----|-----------|---------|---|
| EP | 0 426 571 | 5/1991 | |
| EP | 0 743 514 | 11/1996 | |
| WO | 96 23213 | 8/1996 | |
| WO | WO 96/26432 | * 8/1996 | ........... G01N/21/64 |

* cited by examiner

*Primary Examiner*—Constantine Hannaher
*Assistant Examiner*—Otilia Gabor
(74) *Attorney, Agent, or Firm*—Wenderoth, Lind & Ponack, L.L.P.

(57) ABSTRACT

An optical sensing unit is provided which comprises at least one sample measurement cell, at least one excitation light source acting upon the or each measurement cell to provide one or more sensor fields defining an array of measurement fields, a photoelectric detector array for detecting the intensity of light emitted from the or each measurement cell in response to excitation light, and means for directing light emitted from each measurement field to a respective portion of the photoelectric detector array. The sensing unit may be used in combination with multiplexed waveguide arrays or multiplexed planar cappillary chromatography or electrophoresis chips.

10 Claims, 6 Drawing Sheets

SENSING UNIT PROVIDED WITH SEPARATED DETECTION LIGHT GUIDING

This is a continuation of International Application No. PCT/EP99/03296, filed May 12, 1999, the contents of which are incorporated herein by reference.

This invention relates to an optical sensing unit. More particularly, it relates to a luminescence-based chemical and biochemical optical sensing unit and to the uses thereof.

In human diagnostics, an increasing demand for the detection of extremely low concentrations of biochemically relevant molecules in small sample volumes has triggered research efforts towards more sensitive and selective sensors. Optical sensors are favored because of their chemical stability and ease of fabrication. Bioaffinity sensors based on luminescence excitation schemes combine (bio-)chemical selectivity due to the application of recognition elements specifically binding the analyte molecules, with spatial selectivity originating from evanescent field excitation techniques. Common to the various evanescent field sensing methods that have been developed, interaction with the analyte molecules is restricted to the penetration depth of the evanescent field, thus emphasizing the processes occurring at the sensing surface or within the sensing layer and discriminating processes in the bulk medium.

The combination of fiber-shaped evanescent field sensors with bioaffinity assays, using fluorescent tracer probes for signal generation, has proven capability and is widely used. A detection limit of $7.5 \times 10^{-14}$ M fluorescein-labeled complimentary DNA in a DNA hybridization assay using multimode fibers has been reported. On the other hand, in recent years evanescent field sensors with planar transducer geometries have been adapted for the detection of biomolecules using the principle of effective refractive index changes such as surface plasmon resonance, grating couplers, and interferometers. They are associated with the attractive feature of direct sensing, without the necessity of using any labels. However, the signals of these devices are directly associated with the adsorbed molecular mass which limits the sensitivity of these configurations. Typically, detected concentrations hardly range below $10^{-10}$ M.

Figure 1:
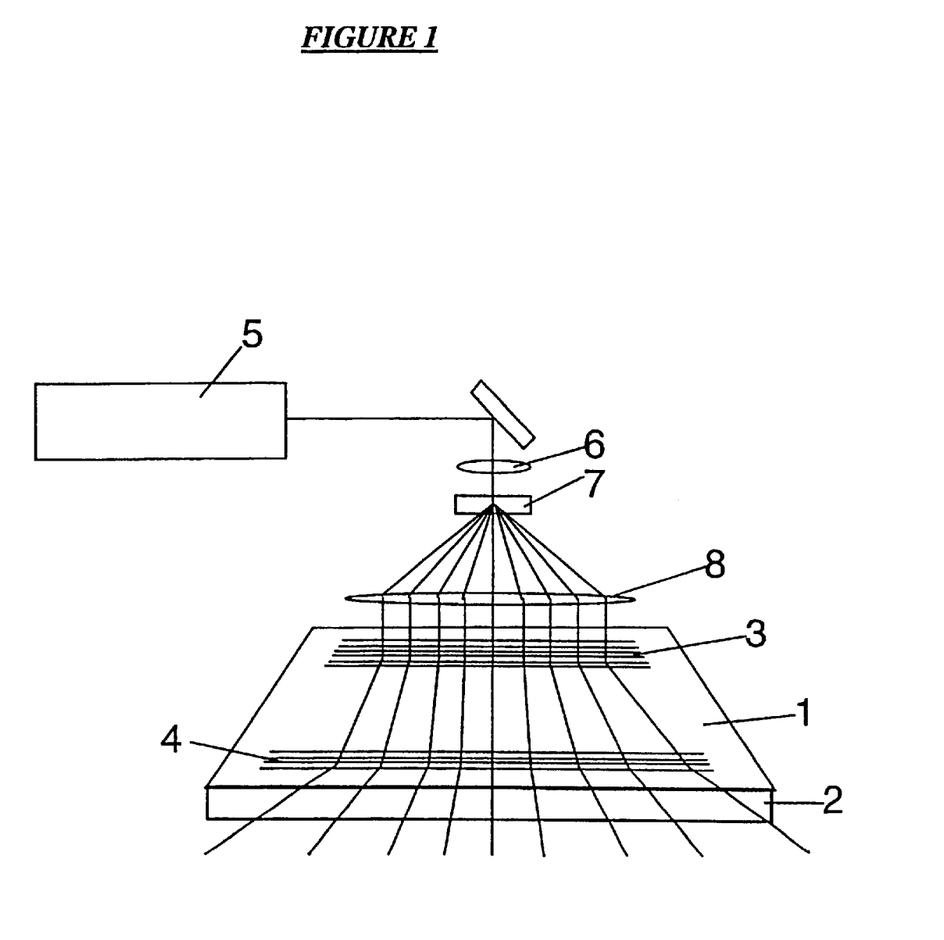
FIG. 1 is a simplified schematic view of a planar waveguide transducer for a bioaffinity sensor and of a multiplexed optical excitation path, using a Dammann grating.

To match the goal of extremely low detection limits in demand by gene probe analysis as well as the diagnostics of diseases and infections, it has been proposed to use single-mode metal oxide waveguides as transducers for luminescence-based bioaffinity sensors. This transducer geometry offers advantages due to ease of production of planar chips, sensor handling, increased excitation efficiency of the luminescence labels, and fluid handling of minute sample volumes. The features of a planar evanescent field transducer for a luminescence detection scheme and the design of a sensor system based on such waveguides are described in a paper by D. Neuschäfer et al, entitled "Planar waveguides as efficient transducers for bioaffinity sensors", Proc. SPIE, Vol. 2836 (1996). The sensor described uses a single-mode planar waveguide consisting of a tantalum pentoxide waveguiding film deposited on a glass substrate. For luminescence detection, in general, a "volume detection" configuration shown in FIG. 1 is used. In this case, the bottom half-sphere part of the luminescence light, which is excited by the evanescent field and then isotropically emitted, is collected underneath the sensor chip, using a high numerical aperture lens or lens system. Two identical interference filters are used for discrimination of excitation light. Signal detection is performed using either photodiodes in combination with high-gain amplifiers, or a selected photomultiplier in combination with a photon-counting unit. As an alternative, the part of the luminescence signal which is coupled back into the waveguiding film may be collected using a second, outcoupling grating (not shown). This is known as "grating detection". The angular separation of outcoupled light of different wavelengths offers the additional feature of simultaneous determination of the- transmitted excitation and the emitted luminescence light intensities, It is also possible to combine the two methods in one device to provide simultaneous "volume" and "grating" detection. A detailed comparison of the two methods is discussed by G. L. Duveneck et al, in a paper entitled "A novel generation of luminescence-based biosensors: single-mode planar waveguide sensors", Proc. SPIE, Vol. 2928 (1996).

In the present application, the term "measurement field" refers to the smallest area of a sensor field capable of discrimination by a photoelectric detector used to detect luminescence. The present invention addresses the need for simultaneous, spatially selective excitation and highly sensitive detection of luminescence signals from an array of measurement fields. Conventional bioaffinity sensors typically rely upon macroscopic imaging of emitted luminescence from a single, large measurement field. A direct transfer of this technique to arrays of measurement fields suffers from inherent optical crosstalk and optical pick-up of background radiation to the extent that the detection limit is often not sufficiently low for many applications. Furthermore, when macroscope optical elements are used to provide a degree of lateral resolution, the distance between the measurement field and the detector array needs to be quite substantial, thereby increasing the overall size of the system. For luminescence detection in extremely small measurement fields and volumes, confocal laser fluorescence microscopy is a very sensitive method. The detection of individual molecules has been demonstrated with excitation areas as small as the diffraction-limited focus of the laser excitation light, i.e. of the order of one wavelength. However, the excitation and detection of a large number of measurement cells in an array requires a lateral translation of the sample with respect to the measuring arrangement to allow sequential measurement of each measurement cell in the array. Accordingly, the time required to receive the signals of a substantial array of measurement fields is prolonged and the relative cost of this type of system itself is expensive due to the size and complexity of the instrument.

According to a first aspect of the present invention, there is provided an optical sensing unit which comprises at least one sample measurement cell, at least one excitation light source acting upon the or each measurement cell to provide one or more sensor fields defining an array of measurement fields, a photoelectric detector array for detecting the intensity of light emitted from the or each measurement cell in response to excitation light, and an array of waveguides or channels for directing light emitted from each measurement field to a respective portion of the photoelectric detector array, characterized in that the array wave-guides or channels have separate beam guiding of the excitation light and emission light for each waveguide or channel.

The present invention addresses the need to improve the ratio of a detected luminescence signal to background "noise" in a luminescence based measurement method. It achieves this by providing a form of beam guiding for light emitted from an array of relatively small measurement fields associated with a number of sensing fields to eliminate optical cross-talk usually associated with conventional macroscopic imaging of adjacent measurement fields. In the preferred examples, an array of waveguides or channels are used with separate beam guiding of the excitation light and emission light for each waveguide or channel.

In one preferred example of the present invention, the one or more sensor fields are provided by the use of a number of planar evanescent field transducers. Preferably, the sensor fields comprise a number of spaced apart optical waveguides, which are preferably arranged in parallel segments. The excitation light is coupled into the array of optical waveguides to establish a number of spatially separated evanescent sensor fields.

Preferably, the or each waveguide is a single-mode metal oxide planar transducer. Where an array of waveguides is provided, they may be integrated on a single substrate. In a preferred embodiment, the spatially separated evanescent sensor fields are established by contacting a continuous metal oxide waveguiding layer, deposited over the whole substrate, with a structured, absorbing surface, having a geometrical arrangement corresponding to the number and pitch of the sensor fields.

The or each measurement cell acts as a conduit or well for a liquid sample. In one preferred example of the present invention, a flow cell housing is provided which is partitioned to form an array of fluid channels having a geometrical arrangement corresponding to the number and pitch of the sensor fields. A preferred form of flow cell is the so-called counter-current flow cell described in the Proceedings on the $\mu$-TAS '96 in Basel, Special Issue 1996 by Analytical Methods & Instrumentation, pp. 158–162. This particular flow cell is adapted to cooperate with a planar transducer substrate to form a fluid-tight compartment.

Preferably, the optical sensing unit comprises a number of optical coupling elements for coupling excitation light into the measurement cells. Preferably, the coupling elements comprise a number of diffraction gratings. The optical sensing unit may also include optical coupling elements for coupling light out of the measurement cells. In particular, in a planar evanescent field transducer configured for grating detection, a second diffraction grating is used to couple out back-coupled luminescence onto the detector array. Alternatively, or in addition, a second diffraction grating can be used to couple out transmitted excitation light onto another detector for reference purposes.

Although a plurality of excitation light sources may be used, one for each measurement cell, preferably a single excitation light source is provided which, if necessary, is multiplexed onto the in-coupling elements to provide an array of parallel light beams. A preferred form of optical multiplexer is a Dammann diffraction grating which, in combination with a suitable optical element such as a lens, is used to provide a parallel set of light beams for establishing a number of sensor fields. Other suitable optical multiplexers include reflection gratings, refractive elements, microlens arrays, microprism arrays, and Fresnel lens arrays.

A laser is a suitable excitation light source, with the appropriate wavelength selected, whether in the form of a laser diode, a solid state laser, or a gas laser. Further, one or more sets of optical shutters may be provided selectively to block excitation light to a number of the measurement cells. Furthermore, the excitation light path may be folded to reduce the size of the optical sensor.

In another preferred example of the present invention, the excitation light beams are not coupled into the waveguiding layer, but launched onto the measurement fields in a configuration similar to classical surface or transmissive illumination. In this example, the amount of luminescence light that is excited in the nearfield of the waveguide (i.e. within about one wavelength from the waveguide surface), is partially coupled into the waveguiding layer and is outcoupled using optical coupling elements, such as diffractive gratings, located adjacent to the measurement fields. One or more arrays of apertures and of microlenses may be provided in the optical path between the outcoupling gratings and the corresponding photoelectric detector array. Additionally, interference filters or an array of interference filters may be arranged in the optical detection path for further discrimination of excitation light.

In yet another preferred example of the present invention, the excitation and detection area or volume of the measurement fields are identical and preferably arranged in a multiplexed configuration of a confocal optical excitation and detection system, with a separate confocal excitation and detection path for each measurement field.

In a further preferred embodiment of the present invention, the multiplexed confocal optical excitation and detection system is constructed around a multiplexed planar capillary chromatography chip, or a planar capillary array electrophoresis chip, with separate excitation and detection for each separation capillary.

In the optical detection arrangement of the present invention, the size and pitch of each measurement field may correspond to the size and pitch of the photoelectric detector array. However, in practice the size of each measurement field is typically somewhat larger than the size of the respective portion of the detector array allocated to it. In the latter case, light emitted from each measurement field is focused onto the respective portion of the detector array.

Preferably, in a "volume detection configuration," the photoelectric detector array is located immediately above or below the measurement cell so as to pick up a component of luminescence light which is radiated isotropically from the measurement fields into space.

Preferably, the optical sensing unit comprises an array of microlenses, which are arranged between the plane of the measurement cell and that of the detector array, to focus light emitted from each measurement field onto a respective portion of the detector array. The array of microlenses may advantageously be integrated with a substrate of the optical sensing unit.

Preferably, the optical detector further comprises an array of apertures adapted to the geometry of the measurement fields to provide optical isolation of emitted light between adjacent measurement fields. The apertures may be substantially planar or may extend orthogonally to the plane of the detector array.

Preferably, the optical sensor further comprises an optical filter or array of optical filters located in a plane between the measurement fields and the detector array to provide signal discrimination.

Examples of suitable photoelectric detectors include multi-channel photomultipliers, CCD arrays, CCD cameras and CMOS devices.

According to a second aspect of the present invention, there is provided a process for determining an analyte by using the present optical sensing unit which comprises introducing a liquid sample into the at least one sample measurement cell, directing a source of excitation light into the at least one measurement cell to establish one or more sensor fields defining an array of measurement fields, guiding luminescence light emitted from each of the measurement fields to a respective portion of the detector array, and detecting the intensity of light emitted by each measurement field, characterized in that the means comprise an array of waveguides or channels with separate beam guiding of the excitation light and emission light for each waveguide or channel.

Preferably, the process comprises the step of directing light into the at least one measurement cell to establish an array of sensor fields.

As will be appreciated by those skilled in the art, the present optical sensor finds a wide variety of applications among those known in the field. Preferred examples include optical determinations of absorbed or excited light in miniaturized and multiplexed chromatographic separation arrays, capillary electrophoresis arrays, or arrays of chemical or biochemical sensors.

The optical sensor according to the present invention is especially suitable for the quantitative determination of biochemical substances in a bioaffinity sensor system. It may be used to test samples as diverse as egg yolk, blood, serum, plasma, lymph, urine, surface water, soil or plant extracts, and a bio- or synthesis process or both. It may also be used, for example, in the quantitative or qualitative determination of antibodies or antigens, receptors or their ligands, oligonucleotides, DNA or RNA strains, DNA or RNA analogues, enzymes, enzyme substrates, enzyme cofactors or inhibitors, lectins and/or carbohydrates.

Examples of the present invention will now be described in detail with reference to the accompanying drawings, in which.

A first example of the present invention is illustrated in FIGS. 1 to 4. A thin-film waveguide 1 (150 nm tantalum pentoxide, refractive index n=2.26 at 633 nm), on a glass carrier 2 (16 mm×48 mm outer dimensions, 0.5 mm thick C7059 glass), is used as a transducer for a bioaffinity sensor. Two sets of diffractive rectangular relief gratings 3 and 4 (two gratings of identical period of 320 nm at a distance of 20 mm, 15 nm grating depth) are fabricated photolithographically in the substrate and transferred into the waveguiding layer upon its deposition on the structured substrate. The first grating 3 is used for the coupling in of the excitation light, whilst the second grating 4 is used for coupling the transmitted excitation light out of the waveguide. The second grating 4 may also be used for coupling back-coupled luminescence light out of the waveguide. As will be described below, in the present invention, fluorescent light, which is excited in the evanescent field of a number of excited measurement fields of the waveguide 1 and radiated isotropically into the space, is detected using a novel detection arrangement.

The excitation light paths are shown diagrammatically in FIG. 1. The excitation light of a HeNe laser 5 (10 mW) is expanded by a lens 6 and impinges onto a Dammann grating 7 as a diffractive optical element. The (non-uniform) periodicity of the Dammann grating 7 is optimized to minimize the intensity of all the even diffraction orders, in particular of the zeroth, i.e. non-deflected order, and to produce as identical an intensity as possible in the other diffraction orders. In this example, 16 component beams are produced in this way, which differ in their intensities by not more than about 5%. An achromatic lens 8 (focal length 160 mm), at whose focal point the Dammann grating 7 stands, is used to produce a bundle of 16 parallel component beams. The divergence of the component beams leaving the Dammann grating 7 and the focal length of the lens 8 are coordinated with each other to obtain a desired pitch (periodicity) of the parallel component beams acting upon in-coupling gratings 3 of the waveguide 1. A suitable pitch is, for example, around 1 mm. FIG. 1 also illustrates the parallel paths followed by the component beams in the waveguide and the coupling out of the transmitted component beams at the second grating 4.

Figure 2:
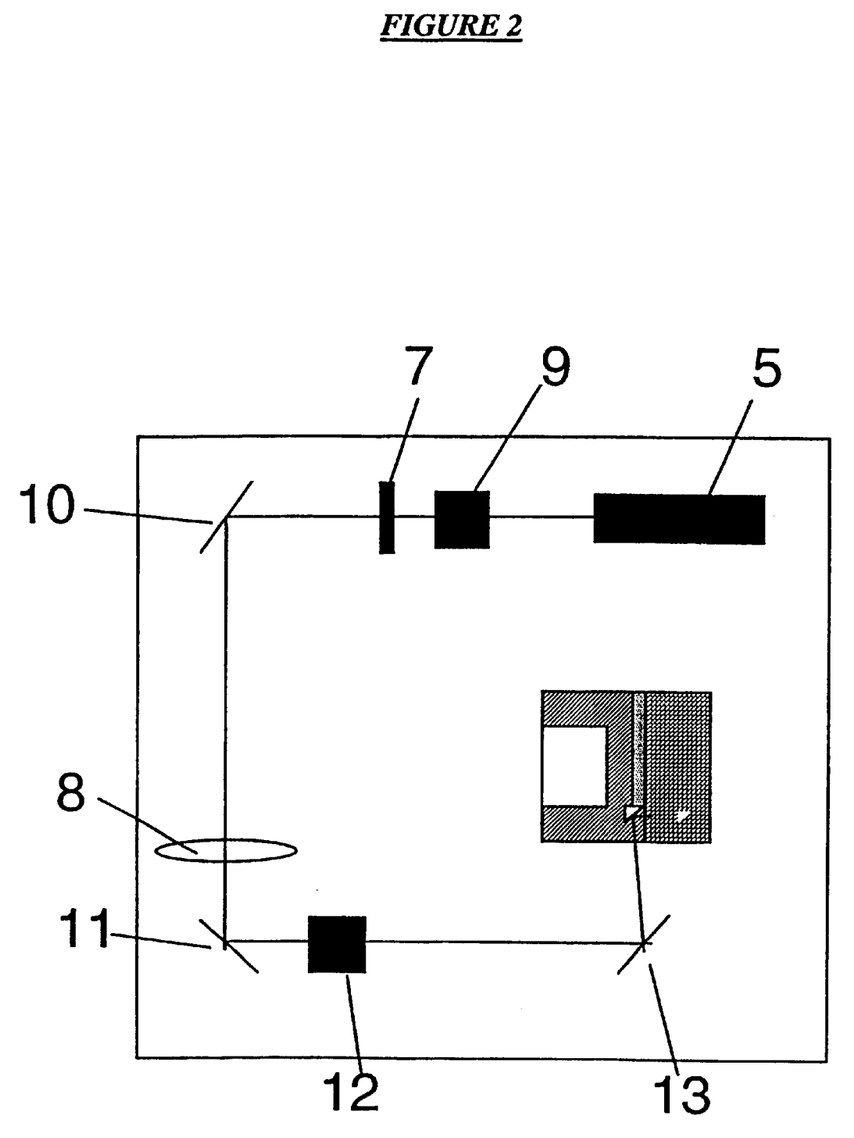
FIG. 2 is a block diagram of an optical set-up for the arrangement of FIG. 1.

FIG. 2 shows the spatial arrangement of the various optical components. A shutter 9 is located between the HeNe laser 5 used as excitation light source and the Dammann grating 7, which is used to block the excitation light path periodically and to release it only when fluorescence intensities of the sample are to be measured. The excitation light path is folded by means of two mirrors 10 and 11 to reduce the overall dimensions of the optical arrangement. A second 16-channel shutter 12 releases alternately the further excitation light path of the even (2, 4, 6 . . . ) and odd (1, 3, 5 . . . ) component beams. This arrangement reduces optoelectronic crosstalk between adjoining detection channels defined by the 16 evanescent sensor fields in the measuring arrangement. The excitation light is diverted onto a prism (not shown), from which it is then directed onto the in-coupling grating or gratings 3 of the waveguide chip. The adjustment of the coupling angle and of the impingement site of the exciting laser component beams takes place in this arrangement at the site of the last folding mirror 13. The detection unit is disposed on the glass substrate-rear side of the waveguide chip and will be described in detail below.

Figure 3:
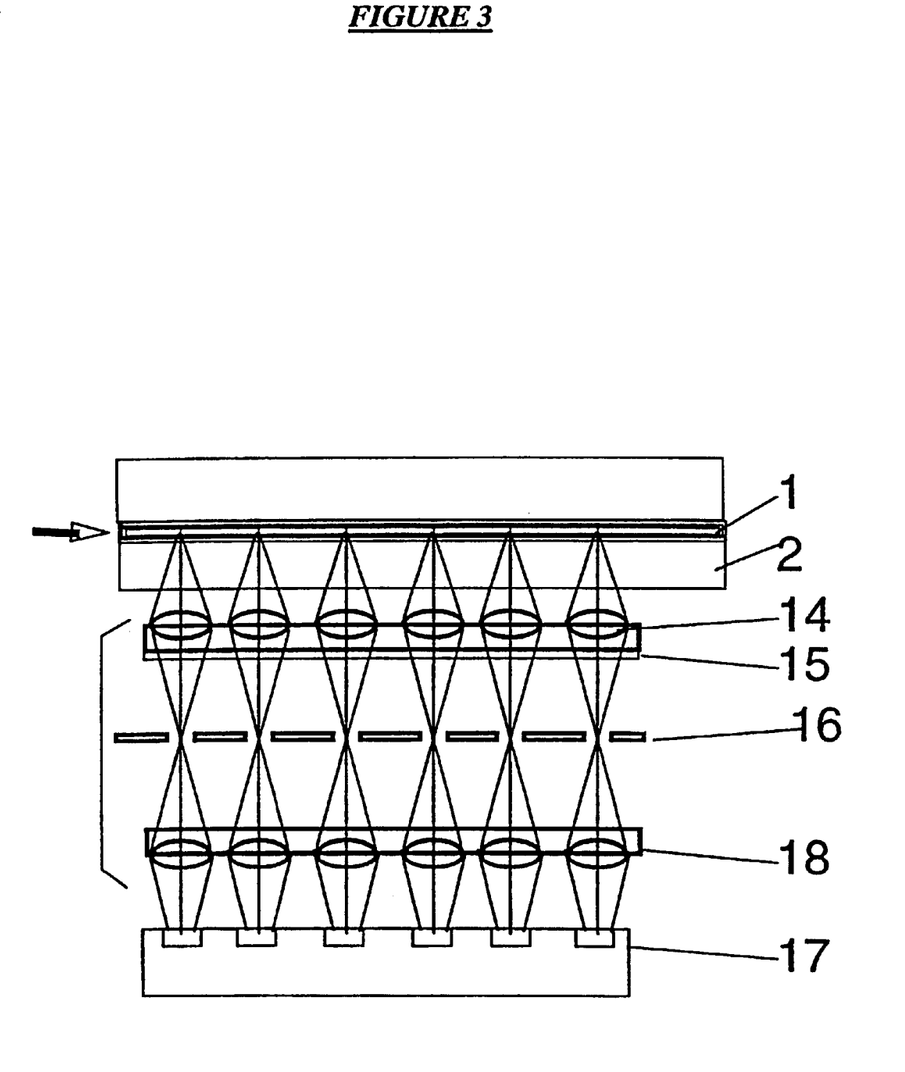
FIG. 3 is a simplified front view of an example of a detection system for a bioaffinity sensor.
Figure 4:
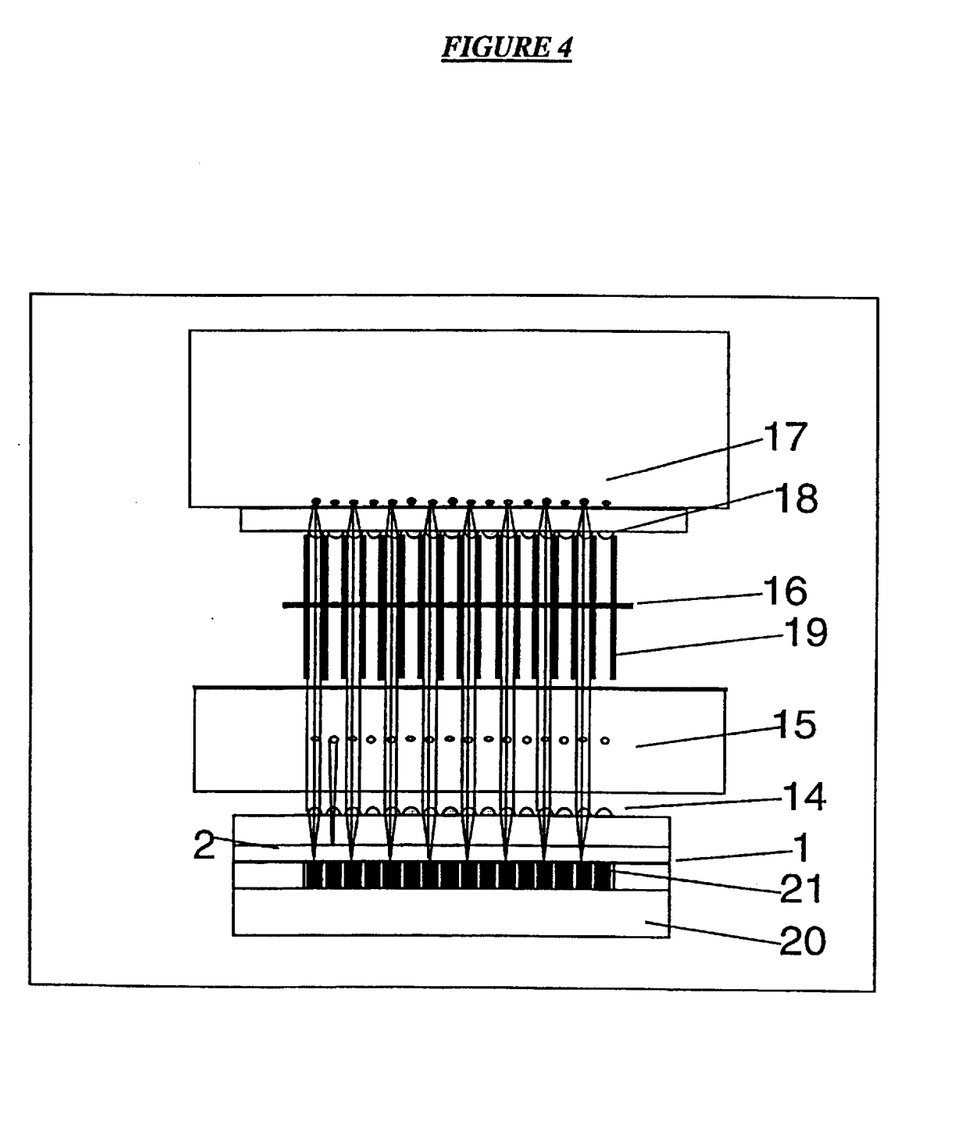
FIG. 4 is a simplified front view of the detection system of FIG. 3.

The general principle of the emission light leaving the separate measurement fields for one waveguide channel (sensor field) being guided via separate ray paths to separate detection elements in a detector array is illustrated in FIG. 3. On the glass substrate-rear side is located, at only a short distance, an array of microlenses 14. Thereafter, the emission light passes through an interference filter array 15 or a continuous interference filter for the discrimination of stray light at the excitation wavelength against the emission wavelength. In this arrangement, if a continuous filter is used, in particular for the diminution of optical crosstalk in the filter, it can be replaced by a filter-array separated by optical barriers. After passage through one or more aperture arrays 16 the detection light is focused onto a the detector array 17 via a further microlens array 18. The detector array 17 is shown in more detail in FIG. 4 and comprises a 16-channel photomultiplier (PMT) with a pitch of 1 mm. Diaphragms 19 may be provided which extend between the interference filter 15 and the 16-channel-PMT 17. The sample flow cell 20 with its array of channels 21 is located beneath the planar transducer.

EXAMPLE

As an experiment, 22-mer oligonucleotides serving as biochemical recognition or capture elements are immobilized by covalent bonding to the reactive groups of an epoxysilane, with which the purified transducer platforms (150 nm tantalum pentoxide on 0.5 mm C7059 glass) had been silanized in the liquid phase. As will be described below, complimentary fluorescence-labelled oligonucleotides are detectable in repeatable cycles of a hybridization assay.

A cycle of the hybridization assay involves:

1. equilibration of the sensor in buffer solution (pH 7.75)/picking up of the background signal;
2. supply of the sample containing the analyte (complimentary 22-mer oligonucleotide 22*-c-Cy5 labelled with cyanine dye Cy5, in a concentration of 1 nanomol/liter, in buffer solution)/picking up of the fluorescence signal during the binding (hybridization) phase;
3. washing with buffer solution/determination of the dissociation rate of the DNA hybrids formed;
4. regeneration of the sensor surface with 10 mM of NaOH/return of the fluorescence signal to the base line; and
5. re-equilibration of the sensor in buffer solution/ checking of the completeness of the regeneration by comparison of the base lines at the start and the end of the assay cycle.

The supply of reagents takes place with the aid of a counter-current cell, as it is described in the Proceedings on the μ-TAS '96 in Basel, Special Issue 1996 by Analytical Methods & Instrumentation, pp. 158–162. The in- and the out-coupling gratings of the biosensor are located, after assembly of the flow cell, whose lid is formed by the transducer surface together with the immobilized identification elements, within a flow channel which is sealed by an O-ring. The inlet for the sample and the various reagents used during the assay cycle is provided to the right of the out-coupling grating, outside the waveguiding area between the coupling gratings, between which the measuring faces are disposed. A buffer counter-stream is directed towards the sample stream flowing in the direction of the in-coupling grating which is admitted to the left of the in-coupling grating, i.e. likewise outside the region of the measuring faces, and is designed to prevent contact between the sample and the in-coupling grating. The common outlet for both streams is located between the two inlets, to the right of the in-coupling grating.

The area incorporated by the flow channel on the transducer platform is sufficient to excite 8 of the 16 component beams produced by the Dammann grating, with a pitch of 1 mm, within the area of the flow cell, to allow the coupled-in laser light to pass in separate stripes through the area up to the out-coupling grating and to excite luminescences in the evanescent field along separated traces of the guided excitation beams propagated in the waveguide. The fluorescence radiated isotropically along the 8 segments is measured during the procedure with the optical detection device described above. The results of the measurement are summarized in Table 1.

Table 1: Results of an oligonucleotide hybridization assay performed on 8 simultaneously excited segments of the planar waveguide transducer platform: Maximum fluorescence signals measured upon hybridization with a 1 nanomolar analyte solution (22*-c-Cy5), noise of background signal, signal:noise ratio, and estimated detection limit for each segment.

| Segment Number | Net Fluorescence Signal [mV] | Background Signal Noise [mV] | Fluorescence Signal/3 × Noise | Detection Limit [pM] |
|---|---|---|---|---|
| 1 | 4279 | 13.8 | 131 | 7.7 |
| 2 | 3354 | 42.8 | 39 | 25.7 |
| 3 | 3525 | 13.0 | 130 | 7.7 |
| 4 | 4927 | 44.2 | 36 | 27.4 |
| 5 | 2303 | 5.5 | 236 | 4.2 |
| 6 | 3684 | 26.3 | 57 | 17.6 |
| 7 | 2923 | 17.3 | 68 | 14.8 |
| 8 | 2419 | 20.9 | 58 | 17.4 |

Apart from varying degrees of scatter of the data, the 8 measurement curves showed substantially the same temporal evolution. The maximum fluorescence intensities for each segment are listed in Table 1. Differences in the results can be explained at least in part by the varying linear velocity of the analyte during its passage through the cell and by the varying density of the immobilized capture elements. In addition, possible variations in the coupling efficiency of the coupling-in grating for the coupling in of the various component beams have a strong influence on the level of the luminescence signals to be observed.

The intensity of the luminescence signals observed is high and from the determined signal-to-noise ratios, it can be estimated that for this miniaturized optical detection device the detection limit, determined by the ratio of maximum signal and signal noise, is achieved with picomolar concentrations (detection limit set as extrapolated fluorescence intensity at threefold noise level).

Figure 5A:
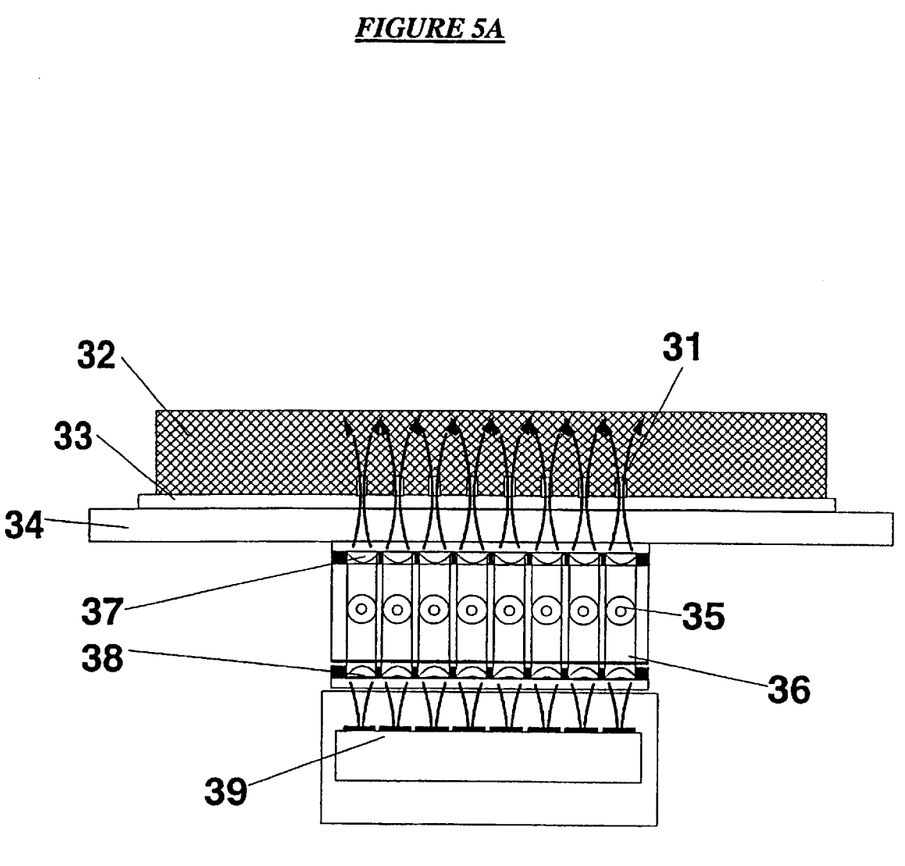
FIGS. 5A and 5B show a simplified schematic view of a capillary electrophoresis-type sensor and optical detection system.
Figure 5B:
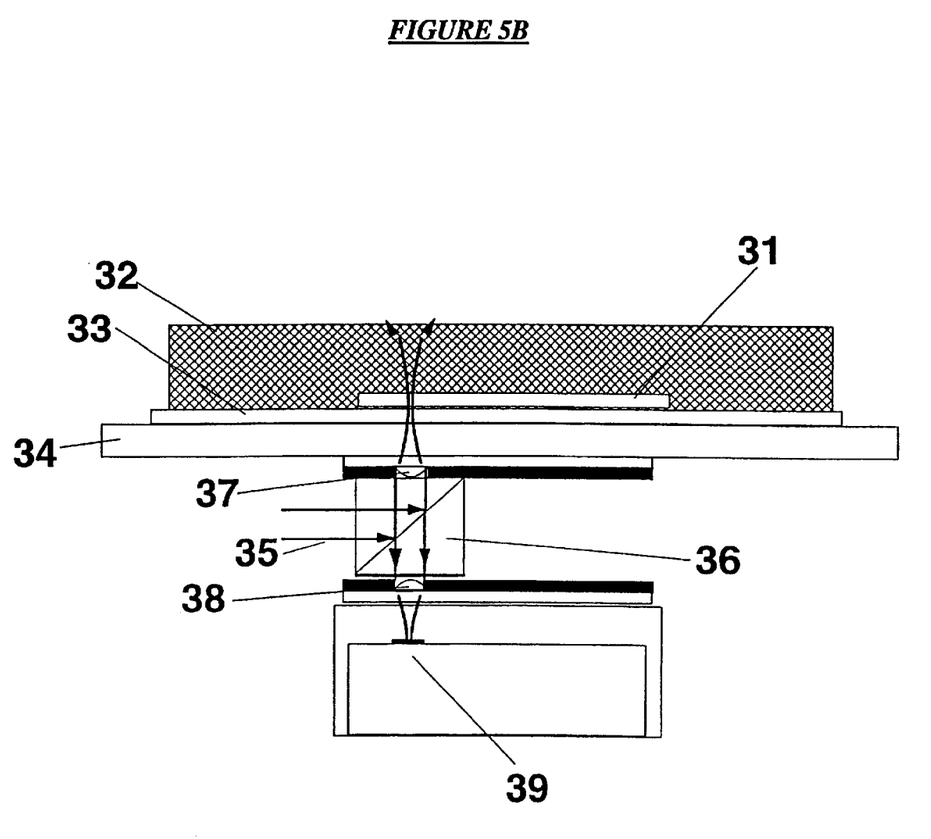

FIGS. 5A and 5B show another example of the present invention adapted specifically for parallel detection in an arrangement of micro-separation channels 31 (capillary electrophoresis, HPLC, or similar). The parallel microchannels can be produced, for example by a simple casting process in a transparent silicone elastomer 32 (PDMS). The cast disc with its channel-type depressions is completed by an unstructured plane PDMS disc 33. Both layers are located on a thin glass plate 34. FIG. 5A shows the overall layout from the perspective of 8 impinging light beams 35 (circles), which are deflected upward by a dichroic mirror 36 positioned through 45° (diagonal interface between two prisms). Each beam is then focused through a microlens 37 onto a respective micro-separation channel. FIG. 5B is a side view of the arrangement showing that a part of the fluorescent light emitted by the analyte is collected with the same lens, and, after passing through a dichroic mirror and an interference filter attached to the underside of the "double prism", is focused through a second microlens 38 onto the photocathode of a photo-multiplier 39.

What is claimed is:
1. An optical sensing unit comprising:
   at least one sample measurement cell;
   at least one excitation light source acting upon said at least one sample measurement cell to provide at least one sensor field defining an array of measurement fields;
   a photoelectric detector array for detecting an intensity of light emitted from said at least one sample measurement cell in response to excitation light; and
   an array of waveguides or channels for directing light emitted from each of the array of measurement fields to a respective portion of said photoelectric detector array, wherein said array of waveguides or channels has separate beam guiding of the excitation light and emission light for each of said array of waveguides or channels.

2. An optical sensing unit according to claim 1, wherein said array of waveguides or channels comprises a number of spaced apart optical waveguides formed on a planar transducer substrate for the at least one sensor field, wherein said optical sensing unit provides separate beam guiding of the excitation light and the emission light for each of said spaced apart optical waveguides.

3. An optical sensing unit according to claim 2, wherein said at least one sample measurement cell comprises a flow cell housing which is partitioned to form at least one fluid channel having a geometrical arrangement corresponding to a number and a pitch of the at least one sensor field.

4. An optical sensing unit according to claim 1, further comprising an array of microlenses which are arranged between a plane of said at least one measurement cell and a plane of said photoelectric detector array to focus light emitted from each of the array of measurement fields onto a respective portion of said photoelectric detector array.

5. An optical sensing unit according to claim 1, further comprising an array of apertures adapted to a geometry of the array of measurement fields to provide optical isolation of emitted light between adjacent measurement fields.

6. An optical sensing unit according to claim 5, wherein said array of apertures extends orthogonal to a plane of said photoelectric detector array.

7. An optical sensing unit according to claim 1, further comprising an optical filter or an array of optical filters located in a plane between the array of measurement fields and said photoelectric detector array to provide signal discrimination.

8. An optical sensing unit according to claim 1, wherein the at least one sensor field comprises a part of a number of channels of a planar capillary chromatography or of a planar capillary electrophoresis chip.

9. A process for determining an analyte by using an optical sensing unit comprising at least one sample measurement cell, at least one excitation light source, a photoelectric detector array, and an array of waveguides or channels, said process comprising:

introducing a liquid sample into the at least one sample measurement cell;

directing excitation light from the at least one excitation light source into the at least one measurement cell to establish at least one sensor field defining an array of measurement fields;

guiding luminescence light emitted from each of the array of measurement fields to a respective portion of the photoelectric detector array via the array of waveguides or channels which have separate beam guiding of excitation light and emission light; and detecting an intensity of light emitted by each of the array of measurement fields with the photoelectric detector array.

10. A process according to claim 9, wherein the array of waveguides or channels comprises an array of waveguides that are used to establish an array of sensor fields, wherein separate beam guiding of the excitation light and the emission light is provided for each waveguide in the array of waveguides, and the excitation light is launched onto the array of measurement fields either in a configuration for transmissive or surface illumination of the array of sensor fields, or by evanescent field excitation.

* * * * *